Dec. 3, 1935. J. H. NICOLAS Plant Pat. 153
ROSE
Filed April 26, 1935
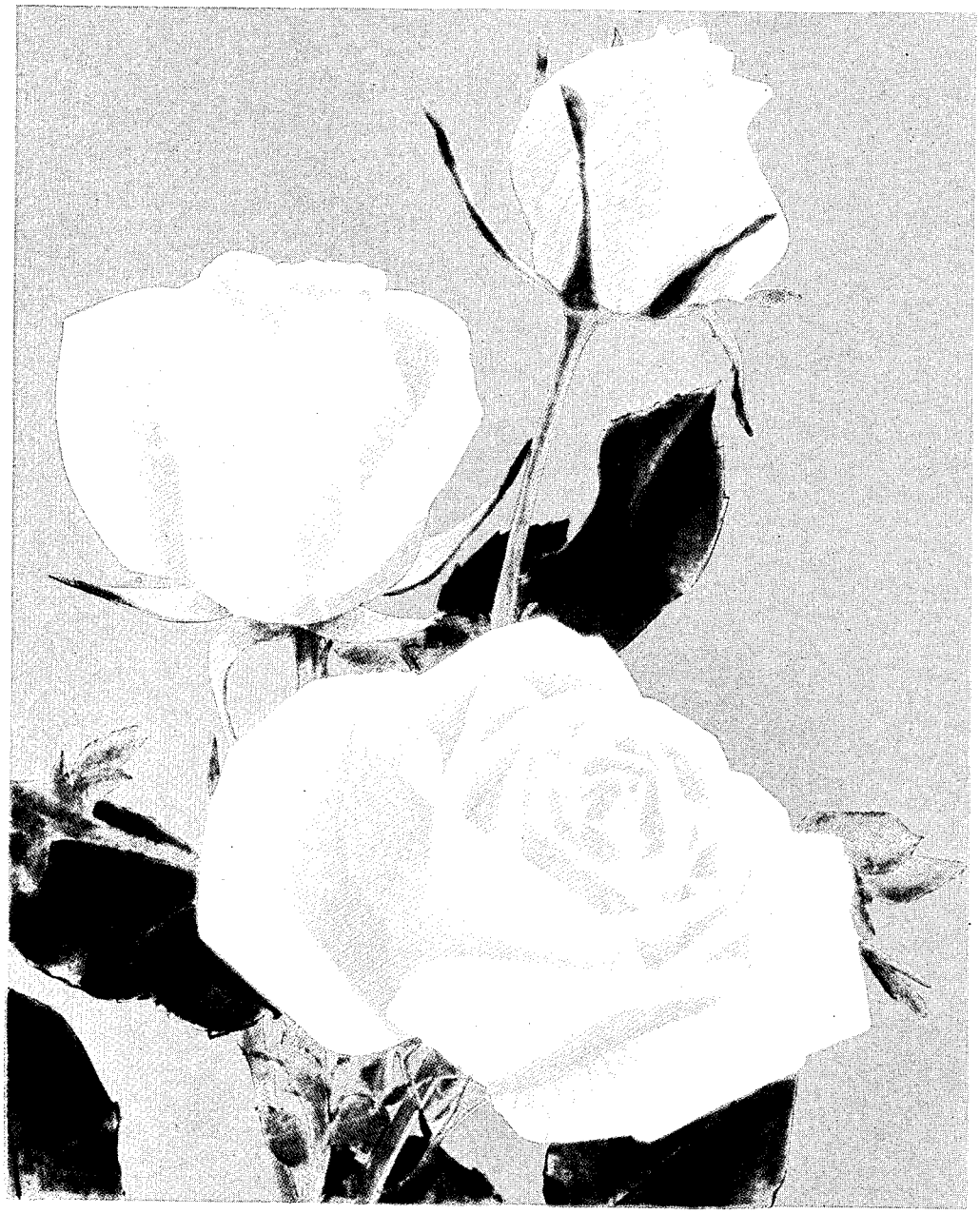
Inventor:
Jean H. Nicolas
By Robb & Robb
attorneys Patented Dec. 3, 1935

UNITED STATES PATENT OFFICE

153

ROSE

Jean H. Nicolas, Newark, N. Y., assignor to Jackson & Perkins Company, Newark, N. Y.

Application April 26, 1935, Serial No. 18,415

1 Claim. (Cl. 47—61)

The present improved plant relates to a discovery which constitutes a new and distinct variety of rose plant, a yellow sport of the well-known "Talisman" which is entirely different from any other yellow sport of said Talisman.

So far as I am aware, it is a fact that all the other yellow sports of Talisman follow the Talisman in all particulars except as to color of the flower and to this extent they are straight dichroisms (sport in color only).

The new variety which I have discovered and developed, however, as hereinafter described, is an extremely rare case of simultaneous dimorphism (sport of form) and dichroism (sport of color). To express it in another way, my new rose is "Souvenir de Claudius Pernet," pollen parent of Talisman, which has come back in almost its entire entity, foliage and bloom, but has retained the floriferousness of Talisman, which is practically double that of Souvenir de Claudius Pernet. I therefore claim that the present variety is a Souvenir de Claudius Pernet in an improved form with the productivity of Talisman.

In view of the greater perfection of form and much greater production of the "Pernet" type, the rose is of great importance to the cut flower industry.

As a garden rose, it is a considerably improved one of the "Pernet" type, insofar as the form of its bloom is concerned, said bloom being more regular and showing no "black heart" (misformed styles and blackened stamens), so much criticized in Souvenir de Claudius Pernet. In other words, it is an improved Pernetiana as to regularity of form, and shows no malformed styles and blackened stamens.

This new variety I have asexually reproduced and have found that its characteristics described are fixed.

The following is a detailed description of the new variety:

Parentage:
Sport of Talisman.

Classification:
*Botanic.*—Pernetiana.
*Commercial.*—Hybrid Tea.

*Flower*

Blooming habit:
Continuous.

Bud:
*Size.*—Very large.
*Form.*—Very long, pointed, ovoid. Unaffected by wet or hot weather.
*Color (Gravereaux color system).*—When sepals first divide saffron yellow. When petals begin to unfurl clear yellow. When half blown—inside of petals clear yellow; reverse of petals clear yellow with darker veins.
*Sepals.*—Branched lightly, and stand up.
*Calyx.*—Shape—funnel. Size—broad. Aspect—smooth. Odor when rubbed—none.
*Peduncle.*—Length—very long. Aspect—rough.
*Color.*—Light green.
*Strength.*—Stiff, heavy.
*Opening.*—Opens well and is not affected by adverse conditions.

Bloom:
*Size.*—Very large; average size when fully expanded 4".
*Borne.*—Singly.
*Stems.*—Long; strong.
*Form.*—When first open high center, globular. Permanence—retains its form to the end.
*Petalage.*—Double (full but open center). Number of petals under normal conditions 30 to 35.
*Color.*—

| | |
|---|---|
| Center of flower<br>Outer petals<br>Base of petals<br>Inside of petals<br>Reverse of petals<br>General tonality from a distance | Solid clear yellow without shadings. |

*Discoloration.*—General tonality at end of first and second day solid clear yellow without shadings; third day slightly paler.

Petals:
*Texture.*—Thick; unaffected by wet or hot weather.
*Appearance.*—Inside satiny; outside satiny.
*Form.*—Round.
*Arrangement.*—Imbricated (regularly arranged shinglelike); petaloids in center, none.
*Persistence.*—Drop off cleanly.
*Fragrance.*—Moderate, fruity (Russet apple).
*Lasting quality.*—On the plant and as a cut flower very long.

Genital organs:
*Stamens, anthers.*—Medium. Color—yellow. Arrangement—regular round styles.
*Stamens. filaments (threads).*—Medium. Color—white.
*Pollen.*—Lemon yellow.
*Styles.*—Loosely separated, length sometimes even, sometimes uneven; medium, heavy.
*Stigmas.*—White color.
*Ovaries.*—Some protruding from calyx.

Fruit:
Variety is seldom fertile.
*Form.*—Round, depressed top.
*Aspect.*—Smooth.
*Color at maturity.*—Russet brown.
*Sepals.*—Caducous (soon falling).

*Plant*

Form:
Bush.
Growth:
Vigorous, branching.
Foliage:
Generally five leaflets.
*Size.*—Very large.
*Quantity.*—Abundant.
*Color.*—New foliage—upper side bronzy. Old foliage—upper side light green; underside lighter green.
*Shape.*—Oval pointed.
*Texture.*—Upper side glossy; underside rough-Ribs and veins impressed.
*Edge.*—Serrated (saw toothed).
*Serration.*—Single, small.
*Leaf stem (rachis).*—Green color; underside prickles.
*Stipules.*—Long; smooth.
*Disease resistance.*—Susceptible to black spot.
Wood:
*New wood.*—Reddish color. Bark—smooth.
*Old wood.*—Green color. Bark—smooth.
Thorns: (Considered as divided into thorns, prickles and short needles)
*Thorns.*—Quantity—on main stalks from base ordinary; on laterals from stalk—few. Form—broad base, medium length, straight. Color when young—green. Position—irregular.
*Prickles.*—Quantity—on main stalks few; on laterals none. Color green.
*Short needles.*—Quantity—on main stalks none and on laterals none.

I claim:

A new and distinct variety of rose plant as shown and described of the Souvenir de Claudius Pernet type, characterized by the improved form of its bloom and great productivity comparable to that of Talisman.

JEAN H. NICOLAS.